(12) United States Patent
Kruiskamp

(10) Patent No.: US 11,357,419 B2
(45) Date of Patent: Jun. 14, 2022

(54) MAGNETIC RESONANCE IMAGING GUIDED THERAPY SYSTEM

(71) Applicant: KONINKLIJKE PHILIPS N.V., Eindhoven (NL)

(72) Inventor: Marinus Johan Kruiskamp, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 780 days.

(21) Appl. No.: 16/317,057

(22) PCT Filed: Jul. 13, 2017

(86) PCT No.: PCT/EP2017/067693
§ 371 (c)(1),
(2) Date: Jan. 11, 2019

(87) PCT Pub. No.: WO2018/011339
PCT Pub. Date: Jan. 18, 2018

(65) Prior Publication Data
US 2019/0298216 A1 Oct. 3, 2019

(30) Foreign Application Priority Data
Jul. 14, 2016 (EP) .................................... 16179538

(51) Int. Cl.
*A61B 5/055* (2006.01)
*A61N 5/10* (2006.01)
(Continued)

(52) U.S. Cl.
CPC ............ *A61B 5/055* (2013.01); *A61N 5/1037* (2013.01); *A61N 5/1049* (2013.01);
(Continued)

(58) Field of Classification Search
CPC .... A61B 5/055; A61N 5/1037; A61N 5/1049; A61N 5/1067; A61N 2005/1055;
(Continued)

(56) References Cited

U.S. PATENT DOCUMENTS 6,268,730 B1 7/2001 Du
7,756,566 B2 7/2010 Machida
(Continued)

FOREIGN PATENT DOCUMENTS

CN 105363138 A 3/2016

OTHER PUBLICATIONS

Breuer et al "Controlled aliasing in parallel imaging results in higher acceleration (CAIPIRINHA) for multi-slice imaging" Magnetic Resonance in Medicine, 53: p. 684-691 (2005).
(Continued)

*Primary Examiner* — Susan S Lee

(57) ABSTRACT

Systems and methods for determining whether a structure of interest is within a predefined region of interest. An example embodiment of a method includes applying a multiband magnetic resonance imaging sequence in order to simultaneously acquire a first slice of magnetic resonance data from a first slice location and a second slice of magnetic resonance data from a second and different slice location. The first slice is positioned near a first side of the region of interest and the second slice is positioned near a second side of the region of interest. The method further includes determining based on the first and second slice of magnetic resonance data and prior knowledge about at least one of the structure of interest and its surroundings whether the structure of interest is within the region of interest.

15 Claims, 4 Drawing Sheets

(51) Int. Cl.
*G01R 33/483* (2006.01)
*G01R 33/54* (2006.01)
*G01R 33/48* (2006.01)
*G01R 33/565* (2006.01)

(52) U.S. Cl.
CPC ....... *A61N 5/1067* (2013.01); *G01R 33/4814* (2013.01); *G01R 33/4835* (2013.01); *G01R 33/546* (2013.01); *G01R 33/56509* (2013.01); *A61N 2005/1055* (2013.01)

(58) Field of Classification Search
CPC ............ G01R 33/4814; G01R 33/4835; G01R 33/546; G01R 33/56509
See application file for complete search history.

(56) References Cited

U.S. PATENT DOCUMENTS

| | | |
|---|---|---|
| 10,124,190 B2 | 11/2018 | Ojha |
| 2002/0115929 A1 | 8/2002 | Machida |
| 2012/0045104 A1 | 2/2012 | Hezel |
| 2013/0035588 A1 | 2/2013 | Shea et al. |
| 2013/0057282 A1 | 3/2013 | Blumhagen et al. |
| 2015/0169836 A1 | 6/2015 | Vahala et al. |
| 2015/0260820 A1 | 9/2015 | Speier |
| 2016/0113570 A1 | 4/2016 | Trausch |
| 2016/0114192 A1 | 4/2016 | Lachaine et al. |
| 2016/0236009 A1 | 8/2016 | Sabczynski et al. |
| 2016/0252596 A1 | 9/2016 | Nielsen et al. |
| 2016/0284103 A1* | 9/2016 | Huang ................ G06T 7/0012 |
| 2016/0310761 A1 | 10/2016 | Li et al. |

OTHER PUBLICATIONS

Setsompop et al. "Blipped-controlled aliasing in parallel imaging for simultaneous multislice echo planar imaging with reduced g-factor penalty" Magn Reson Med. May 2012;67(5):p. 1210-1224.

* cited by examiner

MAGNETIC RESONANCE IMAGING GUIDED THERAPY SYSTEM

CROSS REFERENCE TO RELATED APPLICATIONS

This application is a U.S. national phase application of International Application No. PCT/EP2017/067693, filed on Jul. 13, 2017, which claims the benefit of EP Application Serial No. 16179538.0 filed on Jul. 14, 2016 and is incorporated herein by reference.

FIELD OF THE INVENTION

The invention is in the field of magnetic resonance imaging guided.

BACKGROUND OF THE INVENTION

Motion of a therapeutic target must be taken into account during treatment delivery, like e.g. radiation therapy or high intensity focused ultrasound (HIFU) therapy. Information about the therapeutic target motion can be used for example for gating or position specific therapy plan selection.

Motion gating or tracking motion can also be of relevance in standard diagnostic magnetic resonance (MR) imaging. For example, imaging of the lower chest and upper abdomen requires some method to freeze diaphragmatic motion.

US2015/0169836 describes a method wherein a navigator or a small region of the subject is imaged and wherein this region is registered to a 4D image set of the same subject. This method may for example be used to determine the phase of the subjects breathing.

SUMMARY OF THE INVENTION

It is an object of the invention to improve the information about the position of a structure of interest (e.g. one or more organs and possibly their surroundings, a therapeutic target and/or organs at risk). This object is achieved by a magnetic resonance imaging system configured for determining whether a structure of interest is within a predefined region of interest, wherein the magnetic resonance imaging system comprises
  a memory for storing computer program code means for causing the magnetic resonance system to carry out the following steps:
    applying a multiband magnetic resonance imaging sequence in order to simultaneously acquire a first slice of magnetic resonance data from a first slice location and a second slice of magnetic resonance data from a second and different slice location, wherein the first and second slice location define the region of interest and;
    a determination step for determining based on the first and second slice of magnetic resonance data and prior knowledge about the structure of interest and/or its surroundings whether the structure of interest is within the region of interest; wherein the magnetic resonance imaging system further comprises a processor for executing the computer program code means.
This object is further achieved by a computer program product according to claim 10.

It is an insight of the inventor that while a navigator may be used to obtain information of the subject's breathing phase, it does not provide information related to non-rigid transformation. Non-rigid transformation is for example an issue when treating or imaging a subject's pancreas. Part of the pancreas is located close to the heart, whereas the other part is located close to the liver. As a result, during breathing, the pancreas deforms in a non-rigid way.

Also, navigators may provide some information about the position of a structure of interest. However, this information may be insufficient when a higher accuracy of position determination is required for either imaging or therapeutic purposes.

The simultaneously acquired first and second slice define a region of interest in the body of the subject. Preferably, this region of interest is the region wherein the structure of interest needs to be positioned for subsequent image acquisition or treatment delivery. Preferably, the first slice is positioned near a first side of the region of interest and the second slice is positioned near a second side of the region of interest. By repeatedly simultaneously acquiring the first and second slice it can be more reliably detected if the structure of interest moves outside (or inside) the region of interest. This information can be used for gating of subsequent MRI acquisition or to guide a treatment.

According to embodiments of the invention, the prior knowledge is at least one out of a previous image of at least part of the structure of interest and/or its surroundings or an atlas or shape model of at least part of the structure of interest and/or its surroundings.

According to further embodiments of the invention, the MRI system further comprises a treatment system. This treatment system could for example be a radiotherapy system or HIFU system. A result from the determination step can be used to guide a therapy. For example, this result may be used for gating. In this way treatment is only delivered if the structure of interest is within the region of interest or treatment is only delivered if the structure of interest is not in the region of interest. The latter could for example be relevant when trying to spare an organ at risk.

By means of the invention, in addition to rigid transformations also non-rigid transformation may be detected. In this way the information about the position of the structure of interest may be improved. This information, preferably in combination with positions of organs at risk may be used by the therapy system for guiding a therapy delivery to the patient. This guidance could comprise for example gating, tracking the structure of interest (e.g. by means of moving collimator leaves in case of radiotherapy), selecting a therapy plan from a plurality of pre-calculated therapy plans or real-time calculating of a therapy plan selecting a therapy plan (e.g. a radiotherapy plan) for the subject, which therapy plan takes into account a position and shape of the structure of interest and/or the organs at risk.

According to embodiments of the invention, tracking could be performed by adjusting the first and second slice location to an expected position of the structure of interest. The expected position may be determined based on information acquired during a previous motion cycle and/or by means of a motion model. The result of this tracking may be used for treatment plan selection. Tracking has advantages compared to gating, as tracking may result in reduced treatment delivery times compared to gating.

Simultaneous acquisition of multiple slices could be achieved by means of so-called multiband imaging. Multiband imaging is known from Breuer F A, Blaimer M, Heidemann R M, Mueller M F, Griswold M A, Jakob P M. Magn Reson Med. 2005 March; 53(3):684-91 and Setsompop K, Gagoski B A, Polimeni J R, Witzel T, Wedeen V J, Wald L L. Magn Reson Med. 2012 May; 67(5):1210-24. doi: 10.1002/mrm.23097. Epub 2011 Aug. 19.

At present multiband imaging is used to simultaneously acquire multiple parallel slices. However, in the future the multiple slices may have different orientations as well.

When information is acquired about the rigid and/or non-rigid transformation and/or the position and shape of the structure of interest, this information may be used directly to guide the therapy such that it will result in sufficient dose to the estimated shape and position of the therapeutic target while limiting the dose to the estimated position and shape of the organ(s) at risk. The shape and position of the structure of interest may be estimated based on the acquired information by itself. In addition some (simple) organ motion models may be used.

According to embodiments of the invention the magnetic resonance imaging system is configured for determining the shape and position of the structure of interest by means of image registration between the magnetic resonance imaging data from the multiple slices and a previously acquired 4D image dataset of the structure of interest. This embodiment is advantageous, because it may help to make an accurate estimate of the position and shape of the structure of interest based on the multiple slices acquired.

According to further embodiments of the invention the magnetic resonance imaging guided therapy system is configured for acquiring a second set of multiple slices of the structure of interest. If this is repeated sufficiently often a complete 3D volume of the structure of interest can be covered. This is embodiment is especially advantageous when tracking slowly moving structures.

According to another embodiment of the invention the magnetic resonance imaging guided therapy system is configured for acquiring a second set of multiple slices of the structure of interest wherein the multiple slices in the second set have a different orientation and/or position than the multiple slices in the first set of slices and wherein the magnetic resonance imaging guided radiotherapy system is configured for using the magnetic resonance imaging data from the first and second set of multiple slices for determining the position and shape of the structure of interest. This embodiment is advantageous, because it may allow for more accurate estimation of the position and/or shape of the structure of interest. Preferably the second set of multiple slices is substantially orthogonal to the first set of multiple slices, because this may improve the detection of non-rigid transformation.

These and other aspects of the invention will be apparent from and elucidated with reference to the embodiments described hereinafter.

DETAILED DESCRIPTION OF THE INVENTION

Figure 1:
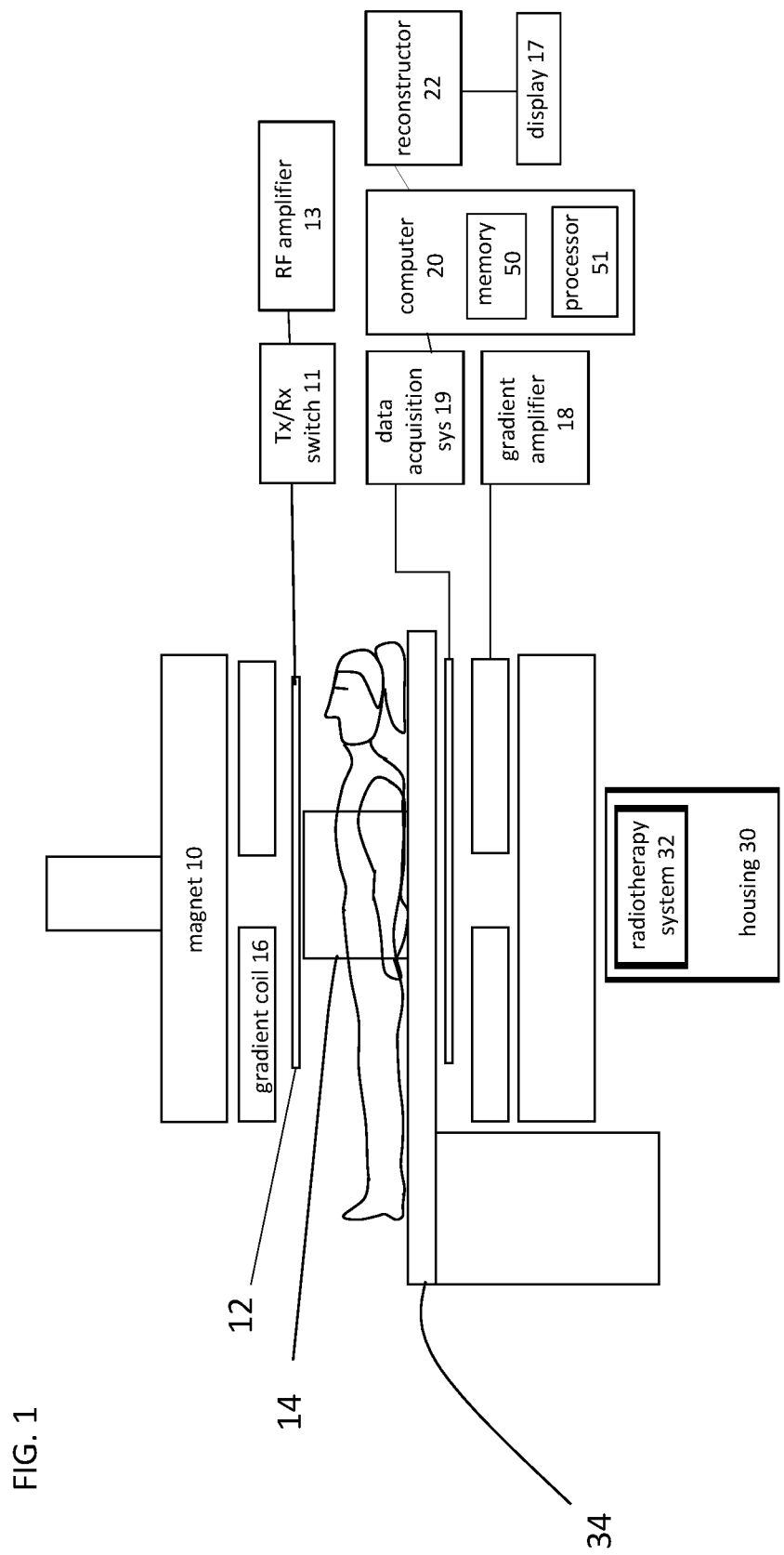
FIG. 1 diagrammatically shows a magnetic imaging guided therapy system according to embodiments of the invention and FIG. 2 diagrammatically shows a method according to an embodiment of the invention and FIG. 3 diagrammatically shows an example of how tracking can be performed according to embodiments of the invention.

FIG. 1 diagrammatically shows a magnetic resonance imaging system comprising a treatment delivery system according to embodiments of the invention.

Figure 2:
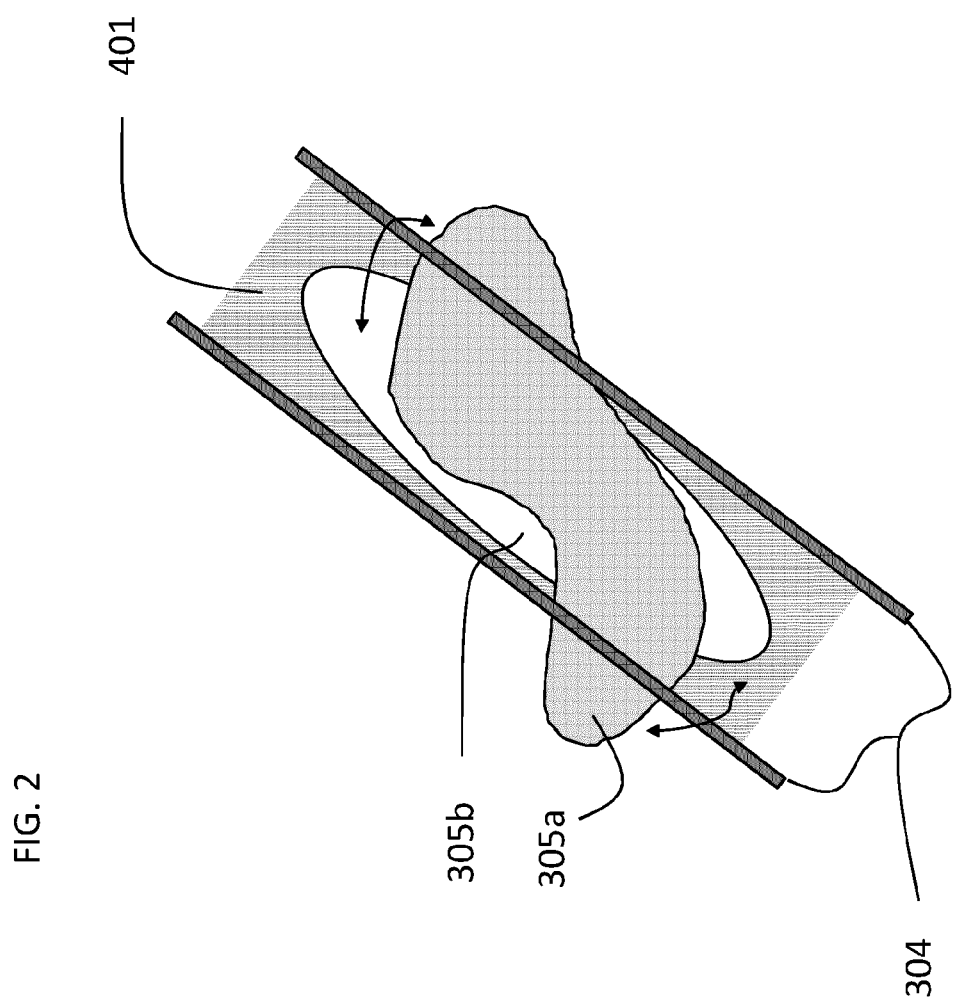
Figure 3:
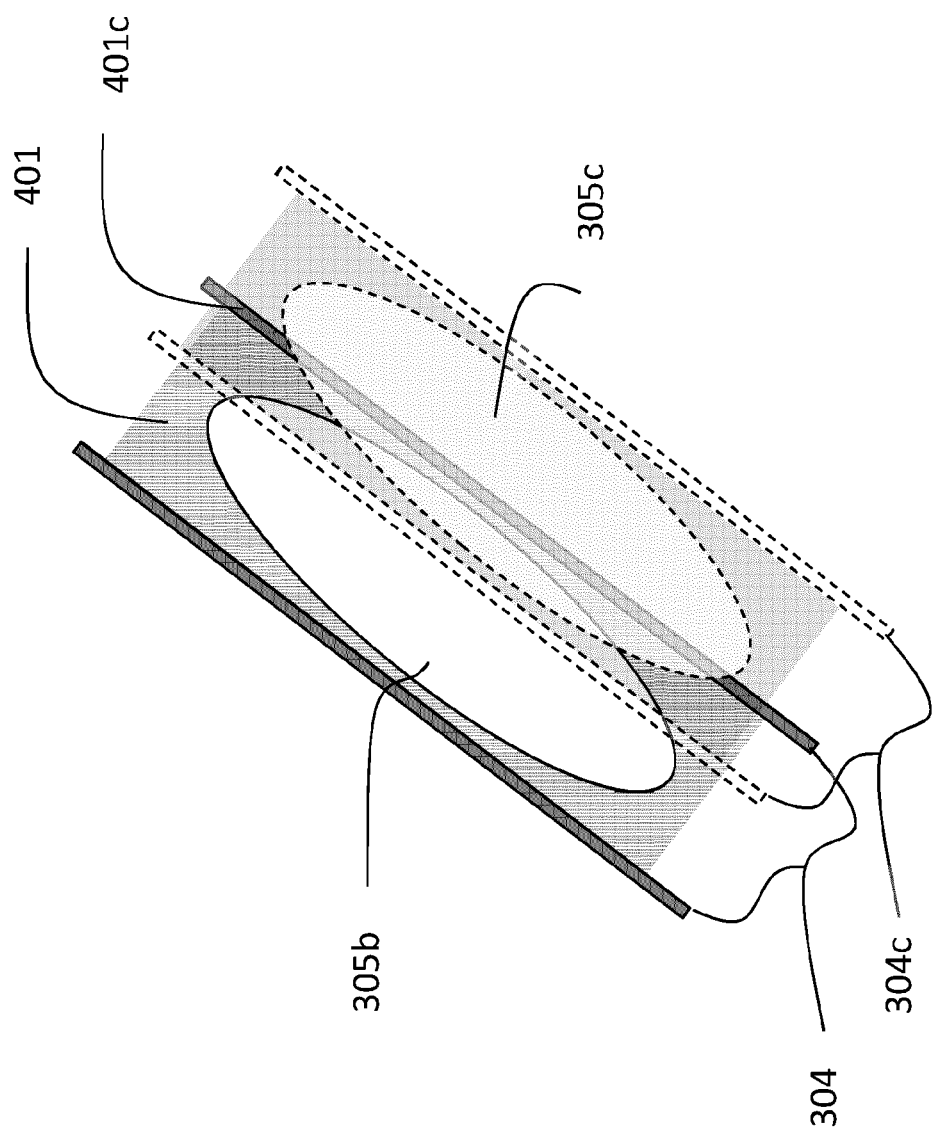

The magnetic resonance imaging system comprises a main magnet 10 which generates a steady homogeneous main magnetic field within the examination zone 14. This main magnetic field causes a partial orientation of the spins in the patient to be examined along the field lines of the main magnetic field. An RF system 12 is provided with one or more RF antennae to emit an RF excitation electromagnetic field into the examination zone 14 to excite spins in the body of the patient to be examined. The relaxing spins emit magnetic resonance signals in the RF range which are picked up by the RF antennae, notably in the form of RF receiving coils 12. The RF system may be coupled to an Tx/Rx switch 11, which in turn is coupled to an RF amplifier 13. Further, gradient coils 16 are provided to generate temporary magnetic gradient fields, notably read gradient pulses and phase encoding gradients. These gradient fields usually are orientated in mutual orthogonal directions and impose spatial encoding on the magnetic resonance signals. Gradient amplifiers 18 are provided to activate the gradient coils to generate the magnetic gradient encoding fields. The magnetic resonance signals picked up by the RF receiver antennae 12 are applied to an MRI data acquisition system 19. The MRI data acquisition system 19 provides the data to a host computer 20, which in turn provides it to a reconstructor 22, which may reconstruct multiple images from the (multiband) data. These data may be displayed on a display 17. The host computer further comprises a memory 50 for storing computer code means for causing the magnetic resonance imaging system to carry out the step of applying the multiband MRI sequence in order to simultaneously acquire the first slice having a of magnetic resonance imaging data having a first slice location and the second slice of magnetic resonance imaging data having a second slice location (FIGS. 2 and 3, 304). The computer code means further causes the magnetic resonance imaging system to determine based on the first and second slice and prior knowledge about the structure of interest and/or its surroundings whether the structure of interest is within the region of interest (FIGS. 2 and 3, 401). The magnetic resonance imaging system further comprises a processor 51 for executing the computer code means.

The magnetic resonance imaging system optionally comprises a treatment delivery system, which is in this example a radiotherapy system 32 including a housing 30 or other support or body supporting a radiation source arranged to move or revolve around the subject. The radiotherapy system 32 may contain a multi-leaf collimator (MLC). The combination of the multi-leaf collimator with the motion of the radiation source around the subject allows the delivery of complex dose distributions by means of for example arc therapy or intensity modulated radiation therapy.

Structure motion can be compensated for by means e.g. gating (both in terms of image acquisition and treatment delivery), tracking the structure of interest, selecting a therapy plan from a plurality of pre-calculated therapy plans or real-time calculating of a therapy plan. Motion can be compensated for by means of hardware and/or software. Examples of motion compensation that can be performed by means of hardware are movement of an imaging table 34 or movement of the leaves in the MLC. An example of motion compensation by means of software could be online recalculation or updating of the radiotherapy plan, e.g. by means of choosing from an atlas of precalculated radiotherapy plans, by means of a radiotherapy plan calculator.

FIG. 2 diagrammatically shows a method according to an embodiment of the invention. In FIG. 2 the first and second slice 304 are used for the purpose of gating. The first and second slice define the region of interest 401. The structure of interest 305 may transform in a non-rigid way as reflected by the structure of interest having a first shape 305a and a deformed shape 305b. The deformation is further indicated in FIG. 2 by means of the arrows. A therapeutic dose will be delivered to the structure of interest 305 as long as the structure of interest is within the volume indicated by 401 (region of interest) (as an example see 305a). Whenever, the structure of interest 305 moves out of volume 401 (region of interest) (see as an example 305b), treatment delivery will be paused.

FIG. 3 diagrammatically shows an example of how tracking can be performed according to embodiments of the invention. In the determination step it may be determined that the structure of interest 401 is in region of interest 401, wherein region of interest 401 is defined by the first and second slice 304. Based on for example a previous motion cycle and/or a motion model for the structure of interest, it may be predicted that the structure of interest will be within region of interest 401c at a subsequent time point. Region of interest 401c can be defined by the first and second slice 304c. By acquiring data from the first and second slice location 304c, it is possible to determine whether the structure of interest has indeed moved into region of interest 401c. If irregularities in the motion pattern of the structure of interest are expected, it may be beneficial to choose the first and second slice location such that they define a larger region of interest. Data acquired from (subsequent) first and second slices may be used to update the motion model.

Figure 4:
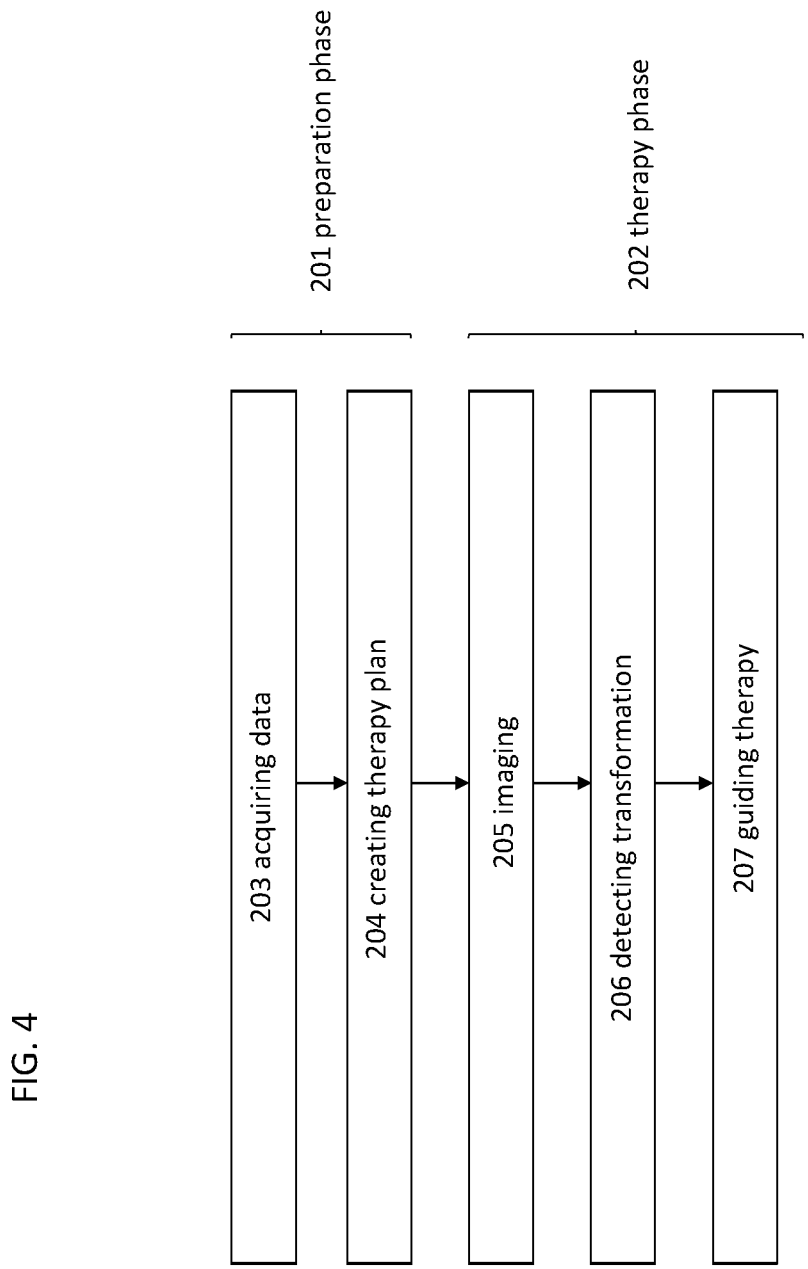
FIG. 4 diagrammatically shows a method according to another embodiment of the invention.

The method shown in FIG. 4 comprises a preparation phase 201 and a therapy phase 202. The preparation phase comprises known method steps and is most likely performed by a system different from a system performing the steps in the therapy phase 202. Prior to therapy a 4D image dataset is being acquired 203 from the therapeutic target (FIGS. 2 and 3 305a, 305b, 30c), and the surrounding organs at risk in order to obtain information about a motion pattern of the therapeutic target and the surrounding organs at risk. Based on the 4D image dataset one or more therapy plans are created 204. The treatment plans are created such that they take into account the motion pattern. This can be achieved in multiple ways. One or more therapy plans could be created such that they can be used during a gating strategy during the therapy phase (example FIG. 2). When using a gating strategy the target will only be irradiated if it is located within a certain area (FIG. 2, 401). The treatment will be paused if the target moves out of this area. Multiple therapy plans could be created such that they take into account several gating strategies. Depending on an actual motion pattern determined when the patient is on the treatment table a suitable therapy plan could be selected from the set of therapy plans. Also a therapy plan can be created that is intended to be used while the therapy system tracks the therapeutic target (example shown in FIG. 3)(e.g. by moving the collimator leaves in case of a radiotherapy system). Alternatively, step 204 and potentially step 203 and 204 could be skipped and the magnetic resonance imaging guided therapy system could be configured to calculate a therapy plan (almost real-time) during treatment delivery.

During the therapy phase 202, multiband imaging 205 is performed on the patient, while he is positioned on the treatment table FIG. 1, 34 of the magnetic resonance imaging guided therapy system. During multiband imaging multiple imaging slices FIGS. 2 and 3, 304 are acquired simultaneously from the target or organ at risk (structure of interest 305). Hereby, the magnetic resonance imaging guided therapy system is configured to more accurately determine the position and shape of the structure of interest. Thereby the magnetic resonance imaging guided therapy system may be also configured to detect non-rigid transformation 206. This information may be used in several ways to guide the therapy 207. Two of these methods are explained in more detail in FIGS. 2 and 3.

Whilst the invention has been illustrated and described in detail in the drawings and foregoing description, such illustrations and description are to be considered illustrative or exemplary and not restrictive; the invention is not limited to the disclosed embodiments.

The invention claimed is:

1. A magnetic resonance imaging system configured to determine whether a structure of interest is within a predefined region of interest, the magnetic resonance imaging system comprising:
a non-transitory computer readable memory for storing computer program code that when executed by a processor causes the magnetic resonance system to:
apply a multiband magnetic resonance imaging sequence in order to simultaneously acquire a first slice of magnetic resonance data from a first slice location and a second slice of magnetic resonance data from a second and different slice location, wherein the first slice is positioned near a first side of the region of interest and the second slice is positioned near a second side of the region of interest; and
determine based on the first and second slice of magnetic resonance data and prior knowledge about at least one of the structure of interest and its surroundings whether the structure of interest is within the region of interest.

2. The magnetic resonance imaging system of claim 1, further configured to generate a result based on the determining whether the structure of interest is within the region of interest and the result is used for gating a subsequent magnetic resonance imaging acquisition.

3. The magnetic resonance imaging system of claim 1, wherein the prior knowledge is at least one out of a previous image of at least part of the structure of interest and/or its surroundings, or an atlas or shape model of at least part of the structure of interest and/or its surroundings.

4. The magnetic resonance imaging system of claim 1, further comprising a treatment delivery system, wherein the treatment delivery system is configured to guide a treatment based on a result of the determination step.

5. The magnetic resonance imaging system of claim 4, wherein the magnetic resonance imaging system is further configured to track the structure of interest, wherein the tracking is performed by adjusting the first and second slice location to an expected position of the structure of interest.

6. The magnetic resonance imaging system of claim 5, further configured to select a therapy plan from a plurality of pre-calculated therapy plans or real-time calculating of a therapy plan based on the tracked position.

7. The magnetic resonance imaging system of claim 1, wherein the first and second slice are parallel slices.

8. The magnetic resonance imaging system of claim 1, further configured to acquire a second set of multiple slices of the structure of interest, wherein the multiple slices in the second set have a different orientation and/or position than the first and second slice.

9. The magnetic resonance imaging system of claim 1, wherein the structure of interest is a therapeutic target or an organ at risk.

10. A computer program product configured to determine whether a structure of interest is within a predefined region of interest, wherein the computer program product comprises program code stored on a non-transitory computer readable such that when the computer program is executed by a processor causes a magnetic resonance system to:

apply a multiband magnetic resonance imaging sequence in order to simultaneously acquire a first slice of magnetic resonance data a first slice location and a second slice of magnetic resonance data from a second and different slice location, wherein the first slice is positioned near a first side of the region of interest and the second slice is positioned near a second side of the region of interest; and determining based on the first and slice of magnetic resonance data and prior knowledge about at least one of the structure of interest its surroundings whether the structure of interest is within the region of interest.

11. The computer program product of claim 10 further including program code for causing the magnetic resonance system to carry out a result based on determining whether the structure of interest is within the region of interest and the result is used for gating a subsequent magnetic resonance imaging acquisition.

12. The computer program product of claim 10, wherein the computer program product further comprises program code for causing a treatment delivery system guide a treatment based on a result of the determination step.

13. The computer program product of claim 10, wherein the computer program product further comprises program code for causing the magnetic resonance system to track the structure of interest, wherein the tracking is performed by adjusting the first and second slice location to an expected position of the structure of interest.

14. The computer program product of claim 13, wherein the computer program product further comprises program code for causing the magnetic resonance system to select a therapy plan from a plurality of pre-calculated therapy plans or real-time calculating of a therapy plan based on the tracked position.

15. The computer program product of claim 10, wherein the structure of interest is a therapeutic target or an organ at risk.

* * * * *